United States Patent
Varma et al.

[11] 3,976,638
[45] Aug. 24, 1976

[54] 16α-ARYLCARBONYLPREGNENES

[75] Inventors: Ravi K. Varma, Belle Mead; Christopher M. Cimarusti, Hamilton, both of N.J.

[73] Assignee: E. R. Squibb & Sons, Inc., Princeton, N.J.

[22] Filed: Oct. 29, 1975

[21] Appl. No.: 626,947

[52] U.S. Cl.................. 260/239.55 R; 260/397.45
[51] Int. Cl.².......................................... C07J 33/00
[58] Field of Search.......................... 260/239.55 R

*Primary Examiner*—Elbert L. Roberts
*Attorney, Agent, or Firm*—Lawrence S. Levinson; Merle J. Smith; Donald J. Barrack

[57] ABSTRACT

Topical and systemic anti-inflammatory activity is exhibited by steroids having the formula

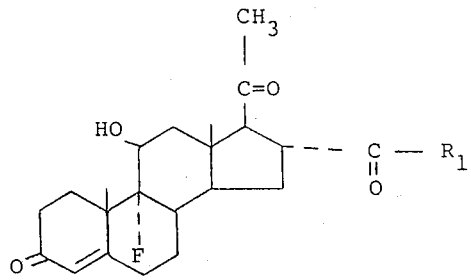

and the 1,2-dehydro derivatives thereof, wherein $R_1$ is phenyl, naphthyl, or substituted phenyl or naphthyl.

9 Claims, No Drawings

16α-ARYLCARBONYLPREGNENES

SUMMARY OF THE INVENTION

Steroids having the formula

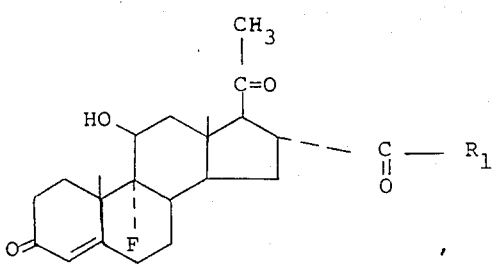

and the 1,2-dehydro derivatives thereof, have useful topical and systemic anti-inflammatory activity. In formula I, and throughout the specification, the symbol $R_1$ can be phenyl, naphthyl, or phenyl or naphthyl substituted with one or two alkyl, alkoxy, halogen or dialkylamino groups.

The term alkyl, as used throughout the specification, refers to straight and branched chain alkyl groups having 1 to 7 carbon atoms.

The term alkoxy, as used throughout the specification, refers to groups having the formula Y—O— wherein Y is alkyl as defined above.

The term halogen, as used throughout the specification, refers to fluorine, chlorine, bromine and iodine.

DETAILED DESCRIPTION OF THE INVENTION

The steroids of formula I are physiologically active substances which possess glucocorticoid and anti-inflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroids of this invention can be used topically in lieu of known glucocorticoids in the treatment of skin conditions such as dermatitis, psoriasis, sunburn, neurodermatitis, eczema, and anogenital pruritus.

When given orally, the compounds of this invention may be used in a daily dosage range of 0.1 to 200 milligrams per 70 kilograms, preferably 0.3 to 100 milligrams per 70 kilograms. If administered topically, the compounds of this invention may be used in the range of 0.01 to 5.0% by weight, preferably 0.05 to 2.0% by weight, in a conventional cream or lotion.

The steroids of this invention can be prepared by reacting a benzaldehyde derivative having the formula

with a steroid having the formula

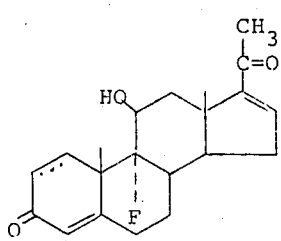

In formula III, and throughout the specification, the dotted line in the 1,2-position of the steroid represents the optional presence of ethylenic unsaturation. The reaction can be run in a polar organic solvent, e.g., dimethylsulfoxide or dimethylformamide, in the presence of sodium cyanide. The reaction is preferably run in an inert atmosphere at a temperature of from about room temperature to about 50°C.

Alternatively, the steroids of formula I can be prepared by first reacting a steroid of formula III with an acetonitrile derivative having the formula

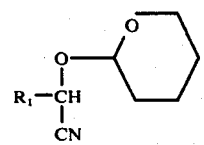

to obtain an intermediate having the formula

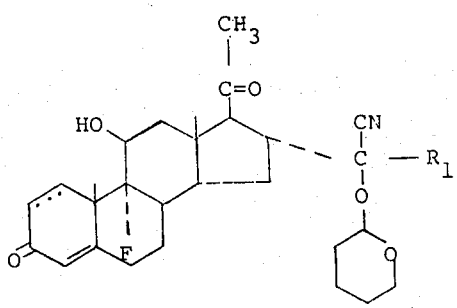

The reaction can be run in a polar organic solvent, e.g., dimethylsulfoxide or dimethylformamide, in the presence of a base such as sodium hydride. The steroid intermediates of formula V are novel, and constitute a part of this invention.

A steroid of formula V can be converted into a product of formula I by treatment with a mineral acid, e.g., hydrochloric acid. The reaction can be run in an organic solvent, preferably a lower alkanol such as methanol.

The starting pregna-4,16-diene of formula III, i.e., 9-fluoro-11β-hydroxypregna-4,16-diene-3,20-dione is well known; see, for example, J. Amer. Chem. Soc., 81, 4956 (1959). The starting pregna-1,4,16-triene of formula III, i.e., 9-fluoro-11β-hydroxypregna-1,4,16-triene-3,20-dione, can be prepared as described in the following examples.

The following examples are specific embodiments of this invention.

EXAMPLE 1

16α-Benzoyl-9-fluoro-11β-hydroxypregn-4-ene-3,20-dione

Method A

A solution of 9-fluoro-11β-hydroxypregna-4,16-diene-3,20-dione (346 mg.) in dry dimethylsulfoxide (6.0 ml.) is added to a stirred solution of benzaldehyde (318 mg.) and sodium cyanide (147 mg.) in dry dimethylsulfoxide under a nitrogen atmosphere at 40°C. After stirring for 1 hour the mixture is diluted with water and extracted with ethyl acetate. The extracts are combined, washed with water, dried over magnesium sulfate, evaporated and the residue is chromatographed on a column of silica gel (35 g.) to yield 64 mg. of 16α-cyano-9-fluoro-11β-hydroxypregn-4-ene-3,20-dione and 100 mg. of 16α-benzoyl-9-fluoro-11β-hydroxypregn-4-ene-3,20-dione.

Method B a. 1-Phenyl-1-tetrahydropyranyloxyacetonitrile

A mixture of mandelonitrile (27 g.) and two equivalents of dihydropyran (18.5 g) is treated with 3 drops of a saturated solution of hydrogen chloride in ether. After about 30 minutes, the mixture is heated to about 100°–110°C and maintained at this temperature for 1 hour. The mixture is cooled and anhydrous potassium carbonate is added. Distillation is used to separate 28 g. of 1-phenyl-1-tetrahydropyranyloxyacetonitrile, boiling point 117°–120°C at 0.40 to 0.45 mm of Hg.

b. 16α-Benzoyl-9-fluoro-11β-hydroxypregn-4-ene-3,20-dione

1-Phenyl-1-tetrahydropyranyloxyacetonitrile (1.3 g.) is added to a suspension of 57% sodium hydride-paraffin (275 mg.) in dry dimethylsulfoxide (20 ml.) in a nitrogen atmosphere. The mixture is stirred at room temperature for 90 minutes to yield a homogeneous solution of the anion. To the anion is added a solution of 9-fluoro-11β-hydroxypregna-4,16-diene-3,20-dione (1.04 g.) in dry dimethylsulfoxide. After 30 minutes, the mixture is poured into water and extracted with ethyl acetate. The extracts are combined, washed with water, dried over magnesium sulfate and evaporated to afford 2.55g. of a gum. This is dissolved in methanol (25 ml.), conc. hydrochloric acid (2 drops) is added and the solution is maintained in a bath at 55°–60°C for 5.0 hours. The methanol is evaporated in vacuo, the residue is dissolved in ethyl acetate, washed with a diluted sodium bicarbonate solution and water, dried over magnesium sulfate and evaporated to afford the crude product as a gum. This is absorbed on a dry column of silica gel (40 g.) and the column is eluted successively with chloroform, ethyl acetate-chloroform (1:9) and ethyl acetate. Crystallization of the material (1.1 g.) eluted with ethyl acetate-chloroform from acetone-hexane affords the analytical specimen (690 mg.), melting point 250°–252°C, dec.

EXAMPLE 2

16α-(4-Chlorobenzoyl)-9-fluoro-11β-hydroxypregn-4-ene-3,20-dione

A solution of 9-fluoro-11β-hydroxypregna-4,16-diene-3,20-dione (346 mg.) in dry dimethylsulfoxide (6.0 ml.) is added to a stirred solution of 4-chlorobenzaldehyde (423 mg.) and sodium cyanide (147 mg.) in dry dimethylsulfoxide at 40°C under a nitrogen atmosphere. After 30 minutes of stirring, the mixture is poured into water and then extracted with ethyl acetate. The extract is washed with water, dried over magnesium sulfate, and evaporated. The residue is subjected to preparative thin-layer chromatography (2.0 mm. silica gel plates, chloroform-ethyl acetate (8:2)) to isolate 200 mg. of 16α-cyano-9-fluoro-11β-hydroxypregn-4-ene-3,20-dione and 200 mg. of 16α-(4-chlorobenzoyl)-9-fluoro-11β-hydroxypregn-4-ene-3,20-dione, melting point 280°–281°C.

EXAMPLE 3

16α-(4-Bromobenzoyl)-9-fluoro-11β-hydroxypregn-4-ene-3,20-dione a. 1-(4-Bromophenyl)-1-tetrahydropyranyloxyacetonitrile 4-Bromobenzaldehyde cyanohydrin (9.1 g.) is dissolved in dry ether (20 ml.), dihydropyran (5.04 g.) is added and the mixture is treated with a saturated solution of hydrogen chloride in ether (0.5 ml.). After 3 hours at room temperature, the mixture is maintained for 1 hour in a bath at 110°C while the ether evaporates. The reaction mixture is cooled, anhydrous potassium carbonate (2.0 g.) is added, and the mixture is distilled in vacuo yielding 2.96 g. of 1-(4-bromophenyl)-1-tetrahydropyranyloxyacetonitrile, boiling point 160°–168°C at 65 mm. of Hg.

b. 16α-(4-Bromobenzoyl)-9-fluoro-11β-hydroxypregn-4-ene-3,20-dione

A solution of 1-(4-bromophenyl)-1-tetrahydropyranylacetonitrile (2.77 g.) in dry dimethylsulfoxide (25 ml.) is maintained in a nitrogen atmosphere and a 57% suspension of sodium hydride in paraffin (455 mg.) is added. After stirring at room temperature for 1 hour, a solution of 9-fluoro-11β-hydroxypregna-4,16-diene-3,20-dione (1.73 g.) in dry dimethylsulfoxide (30 ml.) is added. After 40 minutes the mixture is poured into cold water and extracted with ethyl acetate. The ethyl acetate extracts are combined, washed with water, dried over magnesium sulfate and evaporated to afford a gum (4.8 g.) containing 16α-[1-(4-bromophenyl)-1-tetrahydropyranyloxy-1-acetonitrilo]-9-fluoro-11β-hydroxypregn-4-ene-3,20-dione. This is dissolved in methanol (50 ml.), conc. hydrochloric acid (5 drops) is added and the solution is maintained for 2 hours in a bath at 60°–65°C. Sodium bicarbonate (2.0 g.) is added, the mixture is concentrated in vacuo, then diluted with water and extracted with ethyl acetate. The combined ethyl acetate extracts are washed with water, dried over anhydrous magnesium sulfate, and evaporated to afford the crude product as a gum. This is chromatographed on a column of silica gel (100 g.). The column is eluted with chloroform-hexane (1:1), chloroform, and then with chloroform-ethyl acetate. The fractions eluted with chloroform-ethyl acetate give a solid (2.3 g.) which when recrystallized from ethyl acetate affords 1.14 g. of 16α-(4-bromobenzoyl)-9-fluoro-11β-hydroxypregn-4-ene-3,20-dione, melting point 264°–265°C, dec.

EXAMPLE 4

16α-(4-Bromobenzoyl)-9-fluoro-11β-hydroxypregna-1,4-diene-3,20-dione a. 9-Fluoro-11β-hydroxypregna-1,4,16-triene-3,20-dione i. 9-Fluoro-11β,21-dihydroxypregna-1,4,16-triene-3,20-dione A solution of 2.5 g of 9-fluoro-11β,21-dihydroxypregna-1,4,16-triene-3,20-dione, 21-acetate in 60 ml of methanol and 40 ml of tetrahydrofuran is stirred with 1.0 ml of potassium carbonate at 0°C under nitrogen for 1 hour. After neutralization with 3% acetic acid, the solvent is partially evaporated in vacuo. The slurry is diluted with water and extracted with chloroform. The chloroform solution was dried over anhydrous sodium sulfate and evaporated in vacuo to give 2.0 g of the title compound.

ii. 9-Fluoro-11β, 21-dihydroxypregna-1,4,16-triene-3,20-dione, 21-methanesulfonate A solution of 2.0 g of 9-fluoro-11β,21-dihydroxypregna-1,4,16-triene-3,20-dione in 35 ml of pyridine is stirred at −10°C for 2 hours with 1.1 ml of methanesulfonyl chloride. The solution is poured into cold 5% hydrochloric acid and extracted with chloroform. The chloroform solution was washed with water, dried over anhydrous sodium sulfate and evaporated in vacuo to give 2.4 g of foam. This is dissolved in chloroform and chromatographed on a 25 g-silica gel column. Elution with chloroform-hexane (9:1) gives 2.0 g of the title compound.

iii. 9-Fluoro-21-iodo-11β-hydroxypregna-1,4,16-triene-3,20-dione

A solution of 2.0 g of 9-fluoro-11β,21-dihydroxypregna-1,4,16-triene-3,20-dione, 21-methanesulfonate in 100 ml of acetone is refluxed with 3 g of sodium iodide under nitrogen for about 17 hours. The solid is filtered off and washed with 50 ml of acetone. The filtrate is evaporated in vacuo. The residue is redissolved in chloroform-methanol (9:1), washed with water, dried over anhydrous sodium sulfate and evaporated in vacuo to give 2.0 g of the title compound.

iv. 9-Fluoro-11β-hydroxypregna-1,4,16-triene-3,20-dione

A solution of 1.8 g of 9-fluoro-21-iodo-11β-hydroxypregna-1,4,16-triene-3,20-dione in 135 ml of dioxane is stirred with 90 ml of 5% sodium bisulfite at 105°C under nitrogen for 1.5 hours. The solution is cooled, poured into water, stirred for 30 minutes and filtered. The solid is washed with water and dried in a vacuum oven at 60°C over phosphorous pentoxide to give 780 mg of material. Crystallization from chloroform-methanol gives 420 mg of the title compound, melting point 327°–328°C.

b. 16α-(4-Bromobenzoyl)-9-fluoro-11β-hydroxypregna-1,4-diene-3,20-dione

Following the procedure of Example 3, but substituting 9-fluoro-11β-hydroxypregna-1,4,16-triene-3,20-dione for 9-fluoro-11β-hydroxypregna-4,16-diene-3,20-dione yields the title compound, melting point 285°–286°C.

EXAMPLES 5–10

Following the procedure of Example 1, method A, but substituting the compound listed in column I for benzaldehyde, yields the steroid listed in column II.

| Example | Column I | Column II |
|---|---|---|
| 5 | 3-methylbenzaldehyde | 9-fluoro-11β-hydroxy-16α-(3-methylbenzoyl)pregn-4-ene-3,20-dione |
| 6 | 2-ethoxybenzaldehyde | 16α-(2-ethoxybenzoyl)-9-fluoro-11β-hydroxypregn-4-ene-3,20-dione |
| 7 | 4-dimethylaminobenzaldehyde | 16α-(4-dimethylaminobenzoyl)-9-fluoro-11β-hydroxypregn-4-ene-3,20-dione |
| 8 | 4-fluorobenzaldehyde | 9-fluoro-16α-(4-fluorobenzoyl)-11β-hydroxypregn-4-ene-3,20-dione |
| 9 | 1-naphthaldehyde | 9-fluoro-11β-hydroxy-16α-(1-naphthoyl)pregn-4-ene-3,20-dione |
| 10 | 2-naphthaldehyde | 9-fluoro-11β-hydroxy-16α-(2-naphthoyl)pregn-4-ene-3,20-dione |

EXAMPLES 11–13

Following the procedure of Example 3, but substituting the compound listed in column I for 4-bromobenzaldehyde cyanohydrin, yields the steroid listed in column II.

| Example | Column I | Column II |
|---|---|---|
| 11 | 1-naphthaldehyde cyanohydrin | 9-fluoro-11β-hydroxy-16α-(1-naphthoyl)pregn-4-ene-3,20-dione |
| 12 | 2-chlorobenzaldehyde cyanohydrin | 16α-(2-chlorobenzoyl)-9-fluoro-11β-hydroxypregn-4-ene-3,20-dione |
| 13 | 4-methoxybenzaldehyde cyanohydrin | 9-fluoro-11β-hydroxy-16α-(4-methoxybenzoyl)pregn-4-ene-3,20-dione |

What is claimed is:
1. A steroid having the formula

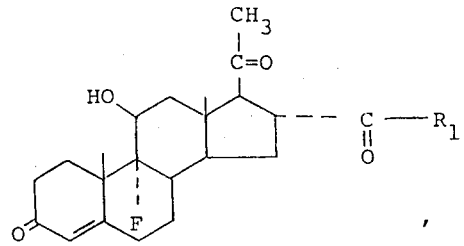

,

3. A steroid in accordance with claim 2 wherein $R_1$ is phenyl or phenyl substituted with halogen.

4. A steroid in accordance with claim 3 wherein $R_1$ is phenyl.

5. The steroid in accordance with claim 1 having the name 16α-benzoyl-9-fluoro-11β-hydroxypregn-4-ene-3,20-dione.

and the 1,2-dehydro derivatives thereof, wherein $R_1$ is phenyl, naphthyl, or phenyl or naphthyl substituted with 1 or 2 alkyl, alkoxy, halogen or dialkylamino groups.

2. A steroid in accordance with claim 1 wherein $R_1$ is phenyl or monosubstituted phenyl.

6. The steroid in accordance with claim 1 having the name 16α-(4-chlorobenzoyl)-9-fluoro-11β-hydroxypregn-4-ene-3,20-dione.

7. The steroid in accordance with claim 1 having the name 16α-(4-bromobenzoyl)-9-fluoro-11β-hydroxypregn-4-ene-3,20-dione.

8. The steroid in accordance with claim 1 having the name 16α-(4-bromobenzoyl)-9-fluoro-11β-hydroxypregna-1,4-diene-3,20-dione.

9. A steroid having the formula

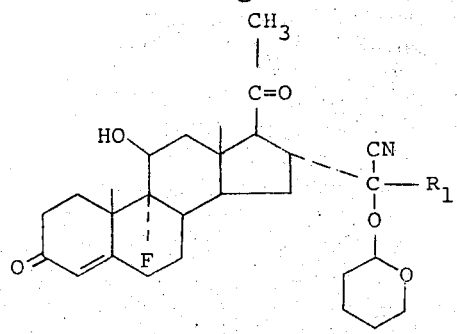

and the 1,2-dehydro derivatives thereof wherein $R_1$ is phenyl, naphthyl, or phenyl or naphthyl substituted with 1 or 2 alkyl, alkoxy, halogen or dialkylamino groups.

* * * * *